United States Patent [19]

Howley et al.

[11] Patent Number: 5,001,296
[45] Date of Patent: Mar. 19, 1991

[54] CATALYTIC HYDRODEALKYLATION OF AROMATICS

[75] Inventors: Paul A. Howley, Woodbury; Stuart S. Shih, Cherry Hill, both of N.J.

[73] Assignee: Mobil Oil Corp., Fairfax, Va.

[21] Appl. No.: 489,994

[22] Filed: Mar. 7, 1990

[51] Int. Cl.$^5$ ............................................. C07C 4/12
[52] U.S. Cl. ................................... 585/489; 585/488; 585/486
[58] Field of Search .................... 585/486, 488, 489

[56] References Cited

U.S. PATENT DOCUMENTS

| | | | |
|---|---|---|---|
| 3,856,872 | 12/1974 | Morrison | 260/668 A |
| 3,945,913 | 3/1976 | Brennan et al. | 208/137 |
| 3,948,758 | 4/1976 | Bonacci et al. | 260/668 A |
| 3,957,621 | 5/1976 | Bonacci et al. | 208/60 |
| 4,021,331 | 5/1977 | Ciric | 585/486 |
| 4,078,990 | 3/1978 | Brennan et al. | 208/64 |
| 4,163,028 | 7/1979 | Tabak et al. | 585/481 |
| 4,188,282 | 2/1980 | Tabak | 208/134 |
| 4,341,622 | 7/1982 | Tabak et al. | 208/66 |
| 4,436,945 | 3/1984 | Koya et al. | 585/488 |
| 4,439,409 | 3/1984 | Puppe et al. | 518/719 |
| 4,560,820 | 12/1985 | Field | 585/488 |
| 4,666,887 | 6/1987 | Fischer et al. | 208/74 |
| 4,738,766 | 4/1988 | Fischer et al. | 208/68 |
| 4,789,457 | 12/1988 | Fischer et al. | 208/68 |
| 4,826,667 | 5/1989 | Zones et al. | 423/277 |

FOREIGN PATENT DOCUMENTS 231860 12/1987 European Pat. Off. .
293032 11/1988 European Pat. Off. .

OTHER PUBLICATIONS

Sarder et al., "Thermal Hydrodealkylation Adapted to Heavy Aromatic Feeds", Oil and Gas Journal, pp. 91 to 99 (Mar. 20, 1989).

*Primary Examiner*—Anthony McFarlane
*Assistant Examiner*—Nhat Phan
*Attorney, Agent, or Firm*—Alexander J. McKillop; Charles J. Speciale; Dennis P. Santini

[57] ABSTRACT

A process is provided for hydrodealkylation of alkylaromatic hydrocarbons to produce benzene or BTX over catalyst comprising a noble metal and a synthetic zeolite, said zeolite characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

18 Claims, 4 Drawing Sheets

CATALYTIC HYDRODEALKYLATION OF AROMATICS

BACKGROUND OF THE INVENTION

This invention relates to the catalytic hydrodealkylation of alkylaromatic compounds to produce a product containing benzene, toluene, and xylene.

Hydrodealkylation (HDA) has been used to convert alkylaromatics to BTX (benzene, toluene, and xylene). Benzene is an especially desired product because of its high demand. Conversely, C$_9$+ aromatics have relatively low value as compared with benzene.

Thermal HDA has been used to convert C$_7$/C$_8$ alkylaromatics to benzene, and remains as an important technology for benzene production in many developing countries. Some studies have indicated that the conventional thermal HDA process can be modified so as to use a C$_9$+ feedstock (see Oil and Gas Journal, Mar. 20, 1989, pp. 91 to 99).

U.S. Pat. No. 4,341,662 discloses BTX production from heavy reformate in substantially the portion in said reformate of single ring aromatics bearing none, one, or two methyl groups by contacting the heavy reformate at 800°–1000° F. with a zeolite of low acid activity.

A process has been developed for catalytic HDA which can produce benzene and BTX from feedstock containing C$_9$+ aromatics, such as, for example, a heavy aromatics plant stream or high boiling point gasoline.

SUMMARY OF THE INVENTION

Provided herein is a process for the catalytic hydrodealkylation of a hydrocarbon feedstock containing at least some alkylaromatic compounds to produce BTX. The process comprises contacting said feedstock under hydrodealkylation conditions with a catalyst composition comprising a noble metal and a particular synthetic zeolite characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

The noble metal component of the catalyst is preferably selected from the group consisting of platinum, palladium, nickel and combinations thereof.

Reaction conditions include a temperature of from about 600° F. to about 1000° F., a pressure of from about 50 to about 500 psig, a hydrogen circulation rate of from about 500 to about 2,000 scf/bbl., and a liquid hourly space velocity of from about 0.5 to about 10 hr$^{-1}$.

BTX or benzene alone can be produced with a high yield from a C$_9$+ aromatic feedstock using a catalyst comprising platinum and the present zeolite in the presence of hydrogen. Conversion and selectivity of the catalytic process of the present invention exceed that of thermal hydrodealkylation under the same conditions.

DETAILED DESCRIPTION OF THE INVENTION

In the present process, a feedstock containing C$_9$+ aromatics can be catalytically hydrodealkylated to produce BTX or benzene alone. The feedstock ideally contains high aromatics content to simplify product separation. The feedstock to the present process may, for example, comprise greater than about 50 mole% C$_6$–C$_{12}$ single-ring aromatics. It may comprise greater than about 50 mole% C$_9$–C$_{12}$ single-ring aromatics.

The process of the present invention is flexible in its capacity to use different feed compositions. For example, the feedstock may be derived from the gasoline produced by the light cycle oil (LCO) upgrading processes such as described in U.S. Pat. Nos. 4,789,457; 4,738,766; and 4,676,887; all of which are herein incorporated by reference, and it may include saturates.

The process of the present invention comprises contacting a feed containing, for example, C$_9$+ aromatics with a synthetic porous crystalline catalyst in the presence of hydrogen under hydrodealkylation conditions. More specifically, hydrodealkylation conditions include a temperature of about 600° F. to about 1000° F., a pressure of from about 50 to about 500 psig, a hydrogen circulation rate of from about 500 to about 2000 scf/bbl, and a liquid hourly space velocity (LHSV) of from about 0.5 to about 10 hr$^{-1}$.

The synthetic porous crystalline composition employed herein as a catalyst comprises a noble metal and crystalline zeolite characterized by an X-ray diffraction pattern including the interplanar d-spacings of Tables A-D, below. Such catalyst is much more active and more selective than thermal HDA for benzene production from heavy aromatics. The presence of noble metal, e.g. platinum, hydrogenates olefins generated by the dealkylation reactions and thus minimizes the recombination of olefins with the BTX. The present catalyst dealkylates alkylbenzenes regardless of chain length, and preserves its activity while processing feeds of lower aromatics content.

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, I/I$_o$ × 100 |
|---|---|
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | M-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, I/I$_o$ × 100 |
|---|---|
| 30.0 ± 2.2 | W-M |
| 22.1 ± 1.3 | W |
| 12.36 ± 0.4 | M-VS |

TABLE B-continued

| Interplanar d-Spacing (A) | Relative Intensity, $I/I_o \times 100$ |
|---|---|
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
|---|---|
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

More specifically, it may be characterized in its calcined form by an X-ray diffraction pattern including the following lines:

TABLE D

| Interplanar d-Spacing (A) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

W=0-20
M=20-40
S=40-60
VS=60-100

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g., silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Preferred metal cations include rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use in the catalyst composition herein, the synthetic porous crystalline material zeolite should be subjected to thermal treatment to remove part or all of any organic constituent present therein.

The zeolite present in the catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the zeolite and/or matrix with which the zeolite may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing the platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal temperature can be performed at a temperature of up to about 925° C.

Prior to its use in the catalyst composition and process of this invention, the zeolite crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, or organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30. wt.% solid $YO_2$. Where YO is silica, the use of a silica source containing at least about 30 wt.% solid silica, e.g., Ultrasil (a precipitated, spray dried silica containing about 90 wt.% silica) or HiSil (a precipitated hydrated $SiO_2$ containing about 87 wt.% silica, about 6 wt.% free $H_2O$ and about 4.5 wt.% bound $H_2O$ of hydration and having a particle size of about 0.02 micron) favors MCM-22 crystal formation from the above mixture and is a distinct difference over the synthesis method disclosed in U.S. Pat. No. 4,439,409. If another source of oxide of silicon, e.g., Q-Brand (a sodium silicate comprised of about 28.8 wt.% of $SiO_2$, 8.9 wt.% $Na_2O$ and 62.3 wt.% $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt.% solid $YO_2$, e.g., silica, and more preferably at least about 40 wt.% solid $YO_2$, e g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desirable to incorporate the zeolite crystalline material with another material, i.e., a binder, which is resistant to the temperatures and other conditions employed in the process of this invention. Suitable binder materials include active and inactive materials and synthetic or naturally occurring zeolite as well as inorganic materials such as clays, silica and/or metal oxides such as alumina. The latter can be either naturally occurring or provided in the form of gelatinous precipitates or gels including mixtures of silica and metal oxides. Use of a binder material in conjunction with the zeolite, i.e., combined therewith or present during its synthesis, which itself is catalytically active may change the conversion and/or selectivity of the catalyst. Inactive materials suitable serve as diluents to control the amount of conversion so that products can be obtained economically and in a controlled fashion without having to employ other means for controlling the rate of reaction.

These materials can be incorporated into naturally occurring clays, e.g., bentonite and kaolin, to improve the crush strength of the zeolite under commercial operating conditions. Good crush strength is an advantageous attribute for commercial use since it prevents or delays breaking down of the catalyst into powder-like materials.

Naturally occurring clays which can be composited with the zeolite crystals include the montmorillonite and kaolin family, which families include the subbentonites, and the kaolines commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

Apart from or in addition to the foregoing binder materials, the zeolite crystals can be composited with an organic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in colloidal form so as to facilitate extrusion of the bound catalyst component(s).

The relative proportions of finely divided crystalline material and inorganic oxide matrix can vary widely with the zeolite content ranging from about 1 to about 95 percent by weight and more usually, particularly when the composite is prepared in the form of beads, in the range of about 2 to about 80 weight percent of the composite.

The stability of the zeolite catalyst may be increased by steaming, with suitable steam stabiization conditions including contacting the catalyst with, for example, 5–100% steam at a temperature of at least 300° C. (e.g. 300°–650° C.) for at least one hour (e.g. 1–200 hours) at a pressure of 100–2,500 kPa. In a more particular embodiment, the catalyst can be made to undergo steaming with 75–100% steam at 315°–500° C. and atmospheric pressure for 2–25 hours.

In order to more fully illustrate the process of this invention and the manner of practicing same, the following examples are presented. In examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample g/100 g of calcined adsorbant. Zeolite MCM-22 always exhibits Equilibrium Adsorption values of greater than about 10 wt.% for water vapor, greater than about 4.5 wt.%, usually greater than about 7 wt.% cyclohexane vapor and greater than about 10 wt.% for n-hexane vapor. These vapor sorption capacities are a notable distinguishing feature of zeolite MCM-22.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec$^{-1}$). The Alpha Test is described in U.S. Pat. No. 3,354,078; in the *Journal of Catalysis*, vol. 4, p. 527 (1965); vol. 6, p. 278 (1966); and vol. 61, p. 395 (1980), each incorporated herein by reference as to that description. The experimental conditions of the test used herein include a constant temperature of 538° C. and a variable flow rate as described in detail in the *Journal of Catalysis*, vol. 61, p. 395.

EXAMPLE 1

One part sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (90% $SiO_2$). The reaction mixture had the following composition, in mole ratios:

| | |
|---|---|
| $SiO_2/Al_2O_3$ = | 30.0 |
| $OH^-/SiO_2$ = | 0.18 |
| $H_2O/SiO_2$ = | 44.9 |
| $Na/SiO_2$ = | 0.18 |
| $R/SiO_2$ = | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the zeolite was measured to be 494 m₂/g.

The chemical composition of the uncalcined material was determined to be as follows:

| Component | wt % |
| --- | --- |
| $SiO_2$ | 66.9 |
| $Al_2O_3$ | 5.40 |
| Na | 0.03 |
| N | 2.27 |
| Ash | 76.3 |
| $SiO_2O/Al_2O_3$, mole ratio | 21.10 |

TABLE E

| Degrees 2-Theta | Interplanar d-Spacing (A) | $I/I^o$ |
| --- | --- | --- |
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of EXAMPLE 1 was tested in the Alpha Test and was found to have an Alpha Value of 224.

EXAMPLES 3-5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| Example | 3 | 4 | 5 |
| --- | --- | --- | --- |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2O/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution was added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table G:

TABLE G

| Product Composition (uncalcined) | | |
| --- | --- | --- |
| C | 12.1 | wt. % |
| N | 1.98 | wt. % |
| Na | 640 | ppm |
| $Al_2O_3$ | 5.0 | wt. % |
| $SiO_2$ | 74.9 | wt. % |
| $SiO_2/Al_2O_3$, mole ratio | 25.4 | |
| Adsorption, wt. % | | |
| Cyclohexane | 9.1 | |
| n-Hexane | 14.9 | |
| $H_2O$ | 16.8 | |
| Surface Area, $m^2/g$ | 479 | |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3g samples of the calcined material ion-exchanged 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

Exchange Ions

| Ionic Composition, wt. % | TEA | TPA | La |
|---|---|---|---|
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
|---|---|
| $SiO_2/B_2O_3$ | = 6.1 |
| $OH^-/SiO_2$ | = 0.06 |
| $H_2O/SiO_2$ | = 19.0 |
| $K/SiO_2$ | = 0.06 |
| $R/SiO_2$ | = 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 240° C. and found to have the following sorption capacities:

| | |
|---|---|
| $H_2O$ | 11.7 wt. % |
| Cyclohexane | 7.5 wt. % |
| n-Hexane | 11.4 wt. % |

The surface area of the calcined crystalline material was measured (BET) to be 405 m$^2$/g. The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/(Al+B)_2O_3$, molar ratio | 25.8 |

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This example illustrates another preparation of the zeolite in which X of the general formula, supra, is boron. Boron acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
|---|---|
| $SiO_2/B_2O_3$ | = 12.3 |
| $OH^-/SiO_2$ | = 0.056 |
| $H_2O/SiO_2$ | = 18.6 |
| $K/SiO_2$ | = 0.056 |
| $R/SiO_2$ | = 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438m$^2$/g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al+B)_2O_3$, molar ratio | 28.2 |

EXAMPLE 14

A portion of the calcined crystalline product of Example 13 was tested in the Alpha Test and found to have an Alpha Value of 5.

EXAMPLE 15

A sample of platinum exchanged MCM-22 catalyst was prepared by providing MCM-22 prepared in accordance with the method described in Example 1 and exchanged with ammonium nitrate. To this was added an aluminum oxide binder. The mixture was mulled, extruded and dried at 250° F. It was then calcined in nitrogen at 1000° F. for 3 hours. After humidification the mixture was exchanged with 1 N ammonium nitrate, dried and calcined again in nitrogen at 1000° F. The mixture was again humidified, exchanged with Pt(NH3)4Cl2 solution for 8 hours, rinsed, dried and calcined at 660° F. in air. This catalyst had the properties shown in Table H.

TABLE H

| Properties of Pt/MCM-22 Catalyst | |
|---|---|
| Composition, wt % | |
| Zeolite* | 65 |
| Platinum | 0.66 |
| Alumina* | 35 |
| Density, g/cc | |
| Packed | 0.45 |
| Particle | 0.73 |
| Real | 2.60 |
| Physical Properties | |
| Pore Volume, cc/g | 0.99 |
| Surface Area, m²/g | 372 |
| Avg. Pore Diameter, A | 81 |

*Prior to platinum addition

EXAMPLE 16

A feed containing 96.8 mole % $C_9+$ aromatics and added hydrogen was contacted with zeolite Pt/MCM-22 catalyst of Example 15. The reaction conditions included a pressure of 200 psig, 2.5 LHSV (liquid hourly space velocity), and 2000 scf/bbl hydrogen. The temperature was varied between 600° F. and 900° F. The resulting product yields in moles are tabulated in Table I. Conversions and selectivities are calculated in accordance with the following formulae:

(1) Based on 100 moles of feed, the $C_7+$ mono-aromatics conversion is defined as:

$$C_7^+ \text{ conversion} = 100 \times \frac{(\text{moles of } C_7^+)\text{feed} - (\text{moles of } C_7^+)\text{product}}{(\text{moles of } C_7^+)\text{feed}}$$

where $C_7+$ is mono-aromatics including $C_7 \ldots C_{12}$ mono-aromatics. Diaromatics (naphthalene and its alkyl derivatives) are not included in $C_7+$.

(2) The benzene selectivity is defined as:

$$\text{Benzene selectivity} = 100 \times \frac{(\text{moles of benzene})\text{product} - (\text{moles of benzene})\text{feed}}{(\text{moles of } C_7^+)\text{feed} - (\text{moles of } C_7^+)\text{product}}$$

(3) Similarly, the $C_9+$ conversion and BTX selectivity as defined as:

$$C_9^+ \text{ conversion} = 100 \times \frac{(\text{moles of } C_9^+)\text{feed} - (\text{moles of } C_9^+)\text{product}}{(\text{moles of } C_9^+)\text{feed}}$$

$$\text{BTX selectivity} = 100 \times \frac{(\text{moles of BTX})\text{product} - (\text{moles of BTX})\text{feed}}{(\text{moles of } C_9^+)\text{feed} - (\text{moles of } C_9^+)\text{product}}$$

TABLE I

Pt MCM-22 Hydrodealkylation of $C_9+$ Aromatics
(2.5 LHSV, 200 psig, 2000 scf/bbl $H_2$)

| Conditions | Feed | Products | | | | | | |
|---|---|---|---|---|---|---|---|---|
| Temp., °F. | | 600 | 700 | 750 | 800 | 825 | 850 | 900 |
| Yields, moles | | | | | | | | |
| $C_1$ | | — | 0.2 | 0.8 | 2.2 | 3.3 | 4.7 | 6.9 |
| $C_2$ | | 0.4 | 7.5 | 19.4 | 42.9 | 57.7 | 69.2 | 69.0 |
| $C_3$ | | 11.1 | 26.4 | 27.2 | 27.1 | 25.9 | 28.7 | 26.0 |
| $C_4$ | | 5.4 | 9.3 | 7.4 | 8.6 | 8.4 | 7.5 | 6.0 |
| $C_5$ | | 2.2 | 4.0 | 2.2 | 4.6 | 4.0 | 1.6 | 1.0 |
| $C_6+$ Saturates | 0.2 | 1.6 | 3.0 | 0.7 | 0.5 | 0.6 | 0.6 | 0.6 |
| Diaromatics | 3.0 | 3.8 | 3.9 | 5.0 | 4.8 | 5.5 | 5.8 | 6.0 |
| $C_6$, Benzene | 4.2 | 16.0 | 31.6 | 33.8 | 39.1 | 39.9 | 45.5 | 45.8 |
| $C_7$, Toluene | 9.2 | 5.8 | 2.7 | 3.7 | 6.0 | 7.8 | 15.1 | 15.4 |
| $C_8$, Xylene | 5.8 | 7.8 | 21.4 | 24.1 | 19.5 | 15.5 | 8.8 | 9.0 |
| $C_9$ Aromatics | 27.8 | 15.8 | 3.4 | 4.4 | 4.0 | 4.3 | 3.7 | 3.7 |
| $C_{10}$ Aromatics | 44.8 | 39.3 | 24.3 | 16.5 | 15.5 | 12.5 | 8.3 | 8.5 |
| $C_{11}$ Aromatics | 4.0 | 3.5 | 1.3 | 0.6 | 0.3 | 0.3 | 0.9 | 0.9 |
| $C_{12}$ Aromatics | 1.0 | 2.1 | 2.7 | 2.7 | 1.7 | 1.6 | 0.9 | 0.9 |
| $C_{13}$ Aromatics | 0 | 0.1 | 0.1 | 0.1 | 0 | 0.1 | 0 | 0 |
| $H_2$ Consum., scf/bbl | | 144 | 370 | 379 | 660 | 796 | 897 | 864 |
| For Benzene Production | | | | | | | | |
| $C_7+$ Conversion, % | | 19.0 | 39.5 | 44.0 | 49.4 | 54.4 | 59.3 | 58.1 |
| Selectivity, % | | 67.0 | 74.8 | 73.7 | 76.8 | 70.8 | 75.5 | 78.0 |
| For BTX Production | | | | | | | | |
| $C_9+$ Conversion, % | | 21.0 | 59.0 | 68.6 | 72.3 | 75.7 | 82.2 | 82.0 |
| Selectivity, % | | 63.8 | 79.7 | 79.5 | 80.9 | 74.8 | 78.9 | 79.8 |

EXAMPLE 17

A thermal hydrodealkylation run was conducted with a feedstock of the same composition as that of Example 16. The reactor contained quartz chips in place of zeolite Pt/MCM-22, and the reactor was conducted at 200 psig, 2.5 LHSV, 5000 scf/bbl $H_2$ at temperatures of 800° F. and 850° F.

The resulting product mole yields, conversion and selectivities are tabulated in Table J.

TABLE J

Thermal Hydrodealkylation of $C_9+$ Aromatics
(2.5 LHSV, 200 psig, 5000 scf/bbl $H_2$)

| Conditions | Feed | Product | |
|---|---|---|---|
| Temperature, °F. | | 800 | 850 |
| Yields, moles | | | |
| $C_2$ | | 0.5 | 0.1 |
| $C_3$ | | 0.6 | 0.1 |
| $C_4$ | | 0.1 | 3.2 |

TABLE J-continued

Thermal Hydrodealkylation of $C_9^+$ Aromatics
(2.5 LHSV, 200 psig, 5000 scf/bbl $H_2$)

| Conditions | Feed | Product | |
|---|---|---|---|
| $C_5+$ | 0.2 | 0.2 | 0.3 |
| $C_6$ Saturates | 3.0 | 3.4 | 3.5 |
| Diaromatics | 3.0 | 3.4 | 3.5 |
| $C_6$, Benzene | 4.2 | 4.9 | 4.8 |
| $C_7$, Toluene | 9.2 | 9.6 | 9.6 |
| $C_8$, Xylene | 5.8 | 6.6 | 9.6 |
| $C_9$ Aromatics | 27.8 | 26.7 | 26.9 |
| $C_{10}$ Aromatics | 44.8 | 43.2 | 43.2 |
| $C_{11}$ Aromatics | 4.0 | 3.8 | 3.8 |
| $C_{12}$ Aromatics | 1.0 | .9 | 1.0 |
| $H_2$ Consumption, scf/bbl | | 19 | 85 |
| For Benzene Production | | | |
| $C_7+$ Conversion, % | | 1.9 | 1.9 |
| Selectivity | | 36.8 | 33.0 |
| For BTX Production | | | |
| $C_9+$ Conversion, % | | 3.9 | 3.5 |
| Selectivity | | 63 | 55.5 |

EXAMPLE 18

Hydrodealkylation conversion of a heavy gasoline made by the LCO upgrading process was conducted with the Pt/MCM-22 catalyst of Example 15. The reaction conditions include an LHSV of 2.5 hr$^{-1}$, a pressure of 200 psig, a hydrogen ratio of 2000 scf/bbl, and temperatures of 850° F. and 900° F.

Table K presents a tabulation of the composition of the feed and the products as well as reaction conditions, conversion and selectivity.

TABLE K

Pt MCM-22 Hydrodealkylation of Heavy Gasoline
(2.5 LHSV, 200 psig, 2000 scf/bbl)

| Conditions | Feed | Products | |
|---|---|---|---|
| Temperature, °F. | | 850 | 900 |
| Yields, moles | | | |
| $C_1$ | | 3.5 | 7.7 |
| $C_2$ | | 19.2 | 29.0 |
| $C_3$ | | 21.6 | 23.9 |
| $C_4$ | | 10.6 | 4.5 |
| $C_5$ | | 5.2 | 1.1 |
| $C_6+$ Saturates | 26.8 | 19.5 | 14.8 |
| Diaromatics | 8.7 | 4.5 | 5.8 |
| $C_6$, Benzene | 3.0 | 10.7 | 9.0 |
| $C_7$, Toluene | 14.8 | 21.9 | 22.6 |
| $C_8$, Xylene | 20.2 | 17.2 | 17.1 |
| $C_9$ Aromatics | 14.1 | 8.4 | 9.0 |
| $C_{10}$ Aromatics | 7.4 | 3.6 | 4.2 |
| $C_{11}$ Aromatics | 4.8 | 1.5 | 1.9 |
| $C_{12}$ Aromatics | 0.2 | 0.1 | 0.1 |
| $H_2$ Consumption, scf/bbl | | 440 | 640 |
| For Benzene Production | | | |
| $C_7+$ Conversion, % | | 14.3 | 10.7 |
| Selectivity | | 87.5 | 90.9 |
| For BTX Production | | | |
| $C_9+$ Conversion, % | | 71.7 | 66.5 |
| Selectivity | | 34.3 | 33.3 |

Figure 1:
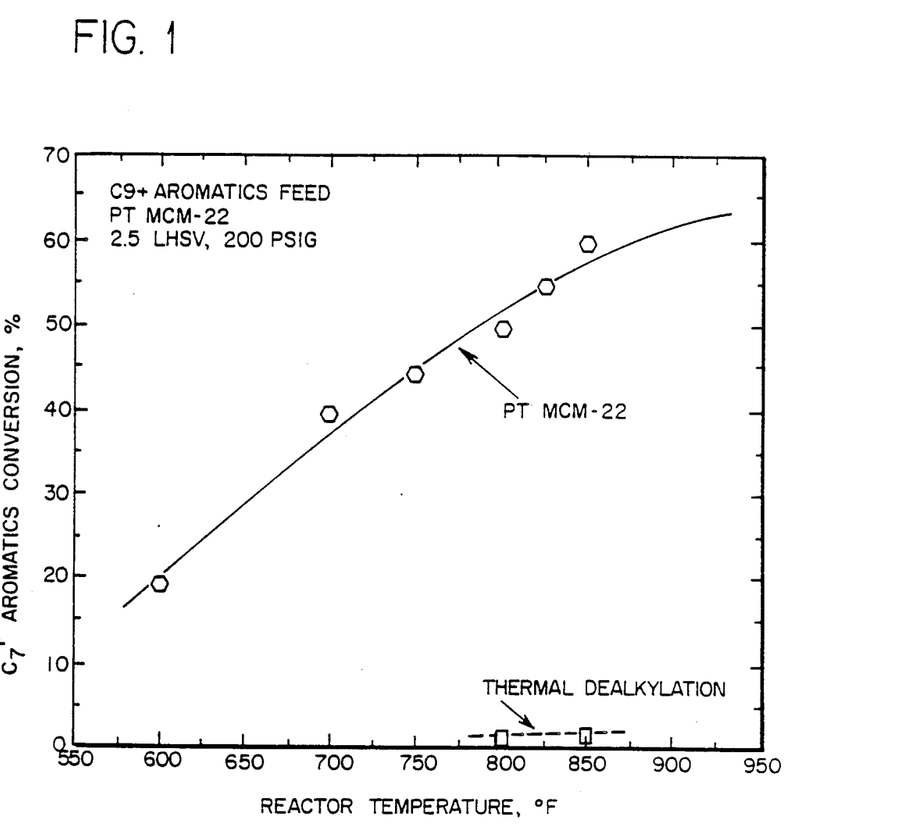
FIG. 1 graphically shows C$_7$+ aromatics HDA conversion for Pt/MCM-22 compared with thermal HDA.

FIG. 1 is a graph showing $C_7+$ aromatics conversion % for the hydrodealkylation reaction of the present invention using Pt/MCM-22 catalyst as opposed to the conversion for the thermal dealkylation method over a temperature range of from about 600° F. to 900° F. Data for this graph is extracted from Tables I and J, infra, as pertaining to benzene production.

Figure 2:
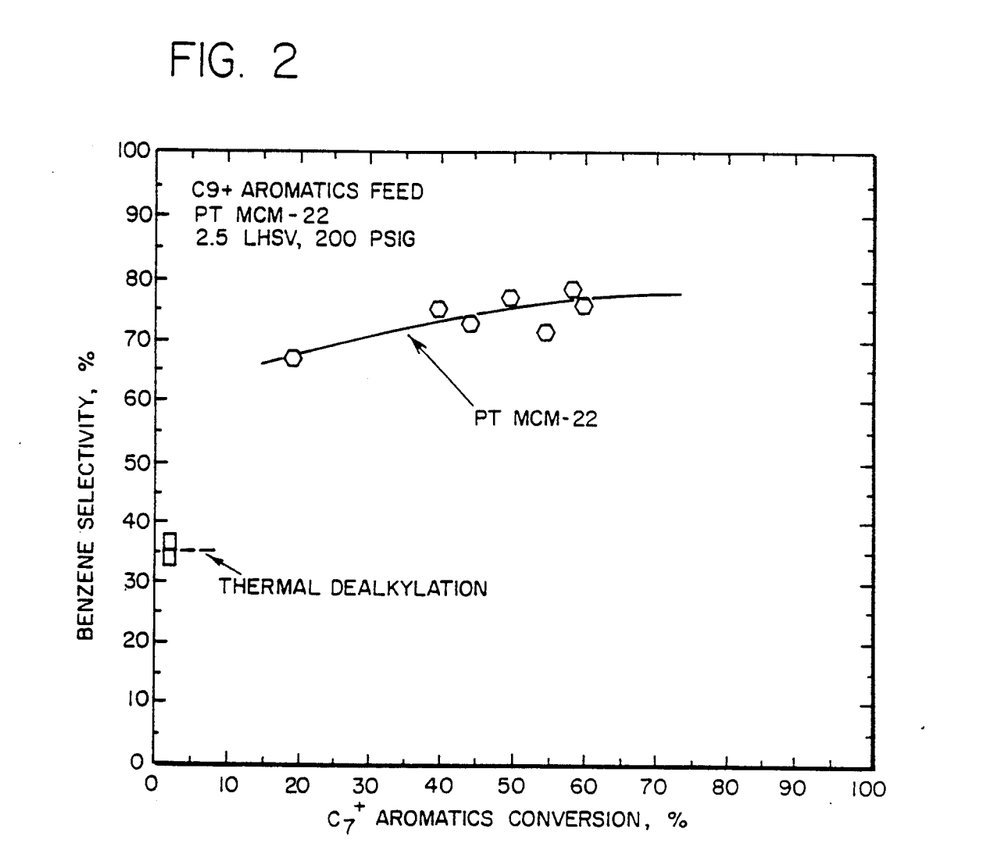
FIG. 2 graphically shows benzene HDA selectivity over a range of C$_7$+ conversions for Pt/MCM-22 compared with thermal HDA.

FIG. 2 is a graph showing the benzene selectivity for the hydrodealkylation reaction of the present invention using Pt/MCM-22 catalyst, in comparison with the benzene selectivity of the thermal dealkylation method, over a range of $C_7+$ aromatics conversion. The data for this graph is extracted from Tables I and J, infra. as pertaining to benzene production.

Figure 3:
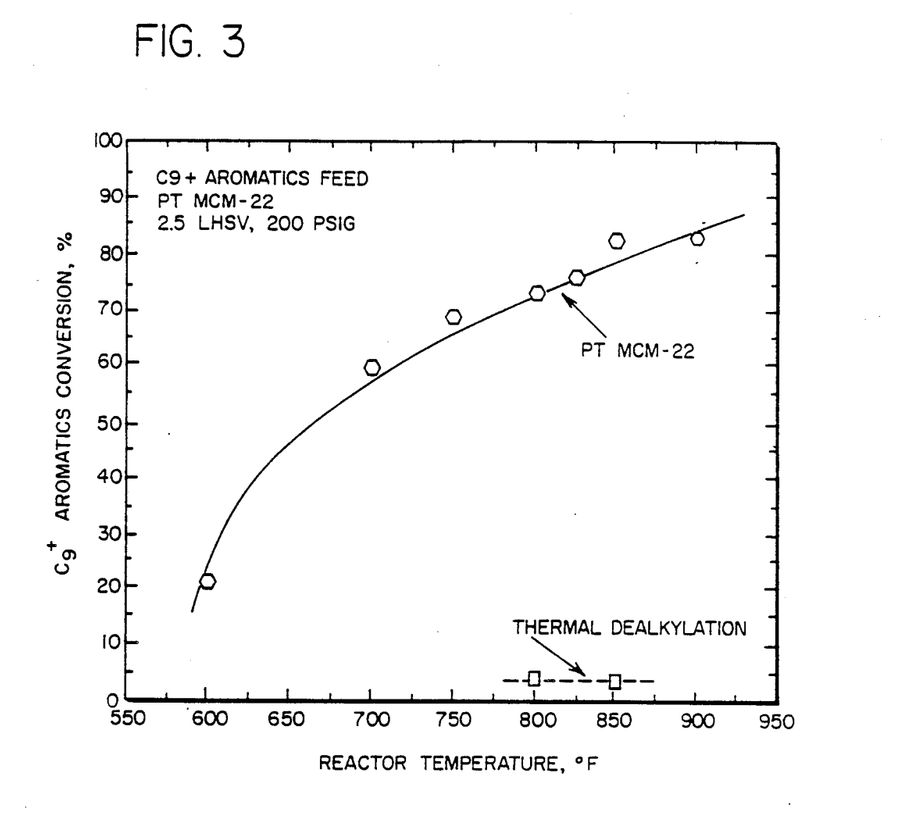
FIG. 3 graphically shows C$_9$+ aromatics HDA conversion for Pt/MCM-22 compared with thermal HDA; and, FIG. 4 graphically shows BTX HDA selectivity over a range of C$_9$+ conversions for Pt/MCM-22 compared with thermal HDA.

FIG. 3 is a graph showing $C_9+$ aromatics conversion of the hydrodealkylation reaction of the present invention using Pt/MCM-22 catalyst in comparison with the conversion of the thermal dealkylation method over a range of temperatures from about 600° F. to 900° F. The data for this graph is extracted from Tables I and J, infra. as pertaining to BTX production.

Figure 4:
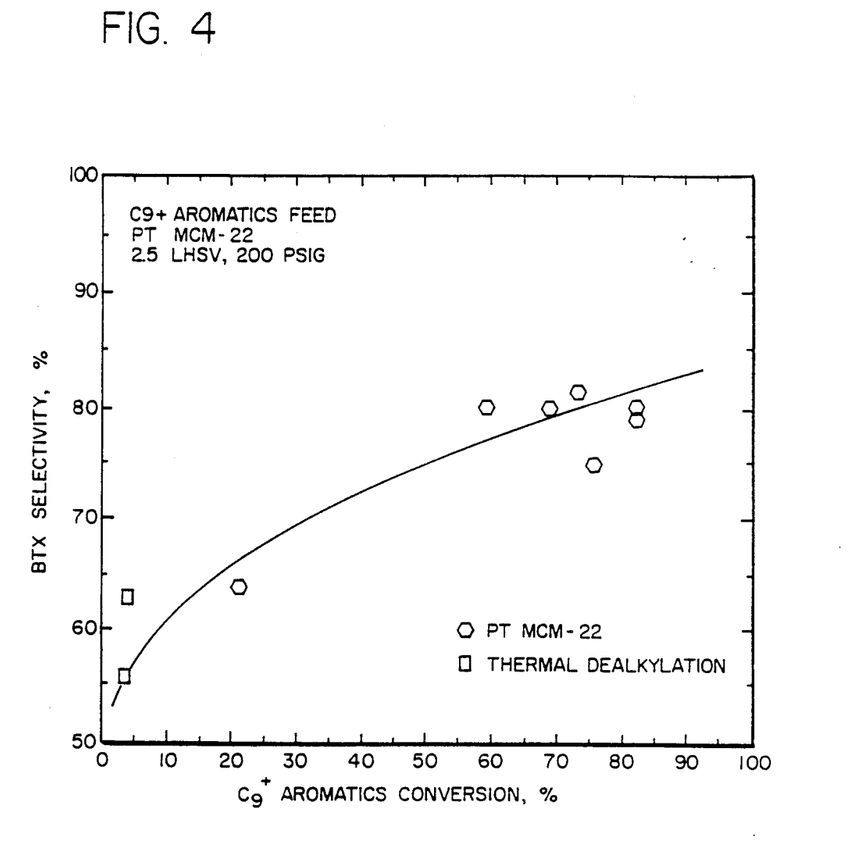

FIG. 4 is a graph showing the BTX selectivity for the hydrodealkylation reaction of the present invention using Pt/MCM- 22 catalyst in comparison with the BTX selectivity for the thermal dealkylation method, over a range of $C_9+$ aromatics conversion. The data for this graph is extracted from Tables I and J, infra, as pertaining to BTX production.

The above-mentioned tables and graphs clearly illustrate that the catalyst for use herein is much more active and more selective than thermal hydrodealkylation for benzene production from heavy aromatics. For example, at 850° F., the catalyst achieved 59.3% conversion of $C_7+$ aromatics and gave a benzene selectivity of 75.5 mole %. At the same conditions, the thermal hydrodealkylation achieved only 1.9% conversion with a benzene selectivity of 33 mole %. Similar conclusions are applied to the BTX production, in which conversion is defined as conversion of $C_9+$ aromatics.

The $C_9+$ aromatics feed used in the above examples has a total aromatics purity of 96.8 mole %. This high aromatics purity is desirable because it simplifies product separation and purification. However, to maximize process flexibility, it is also desirable to have a process that can handle a wide range of feed compositions. To demonstrate the feed flexibility of this proposed process, a $C_6+$ gasoline produced from an LCO upgrading process was evaluated in Example 18. This gasoline consisted of 64.5 mole % $C_6$-$C_{12}$ aromatics, 26.8 mole % saturates, and 8.7 mole % diaromatics. The results show that the catalyst for use herein maintains its effectiveness for processing feeds with lower concentration of aromatics. For example, at 850° F. and 2.5 LHSV, processing with the present catalyst increased the benzene content of the $C_6+$ gasoline from 3.0% to 10.7% moles based on feed. Similarly, the overall BTX concentration increased from 38 moles to 49.8 moles (Table K). These results also indicate that the catalyst for use herein can dealkylate alkyl benzenes regardless of chain length of the alkyl groups.

What is claimed is:

1. A process for catalytic hydrodealkylation of a hydrocarbon feedstock containing alkylaromatic compounds to provide a hydrodealkylated product containing benzene, said process comprising contacting said feedstock under hydrodealkylation conditions with a catalyst composition comprising a metal selected from the group consisting of noble metal, nickel, and combinations thereof, and a synthetic zeolite characterized by an X-ray diffraction pattern including values substantially as set forth in Table A of the specification.

2. The process of claim 1 wherein said zeolite is characterized by an X-ray diffraction pattern including values substantially as set forth in Table B of the specification.

3. The process of claim 1 wherein the zeolite is characterized by an X-ray diffraction pattern including values substantially as set forth in Table C of the specification.

4. The process of claim 1 wherein the zeolite is characterized by an X-ray diffraction pattern including values substantially as set forth in Table D of the specification.

5. The process of claim 1 wherein the synthetic zeolite has a composition comprising the molar relationship:

$$X_2O_3:(n)YO_2$$

wherein X is a trivalent element selected from the group consisting of aluminum, boron, iron and gallium, Y is a tetravalent element selected from the group consisting of silicon and germanium, and n is at least about 10.

6. The process of claim 1 wherein said synthetic zeolite has been treated to replace original ions, at least in part, with an ion or mixture of ions selected from the group consisting of hydrogen, rare earth metals, and metals of Groups IIA, IIIA, IVA, IB, IIB, IIIB, IVB, VIB and VIII of the Periodic Table.

7. The process of claim 1 wherein said noble metal is selected from the group consisting of platinum, palladium, and combinations thereof.

8. The process of claim 1 wherein said feedstock comprises greater than about 50 mole % $C_6$-$C_{12}$ single-ring aromatics.

9. The process of claim 1 wherein said hydrodealkylation conditions include a temperature of from about 600° to about 1000° F., a pressure of from about 50 to about 500 psig, a hydrogen circulation rate of from about 500 to about 2,000 scf/bbl, and a space velocity of from about 0.5 to about 10 $hr^{-1}$.

10. The process of claim 1 wherein said feedstock comprises more than about 50 mole % $C_9$-$C_{12}$ single-ring aromatics.

11. The process of claim 1 wherein the feedstock comprises a high boiling point gasoline derived from a light cycle oil upgrading process.

12. The process of claim 1 wherein the hydrodealkylated product additionally contains toluene and/or xylene.

13. The process of claim 1 wherein said process is further characterized by $C_7+$ aromatics conversion of greater than about 19% for benzene production.

14. The process of claim 1 wherein said process is further characterized by a $C_9+$ aromatics conversion of greater than about 21% for benzene, toluene, and xylene production.

15. The process of claim 1 wherein said process is further characterized by a $C_7+$ aromatics conversion of greater than about 10.7% for benzene production from a feed containing up to about 26.8 mole % saturated hydrocarbons.

16. The process of claim 1 wherein said process is further characterized by a $C_9+$ aromatics conversion of over about 66.5% for benzene, toluene, and xylene production from a feed containing up to about 26.8 mole % saturated hydrocarbons.

17. The process of claim 1 wherein said zeolite is composited with a matrix material.

18. The process of claim 17 wherein said matrix material is selected from the group consisting of silica, alumina, zirconia, titania, beryllia, magnesia, thoria, and combinations thereof.

* * * * *

UNITED STATES PATENT AND TRADEMARK OFFICE
CERTIFICATE OF CORRECTION

PATENT NO. : 5,001,296
DATED : March 19, 1991
INVENTOR(S) : P.A. Howley et al.

It is certified that error appears in the above-identified patent and that said Letters Patent is hereby corrected as shown below:

Col. 10, Table F, line 14, "adsorotion" should be --adsorption--

Signed and Sealed this

Nineteenth Day of January, 1993

Attest:

DOUGLAS B. COMER

Attesting Officer      Acting Commissioner of Patents and Trademarks